Figure 1:
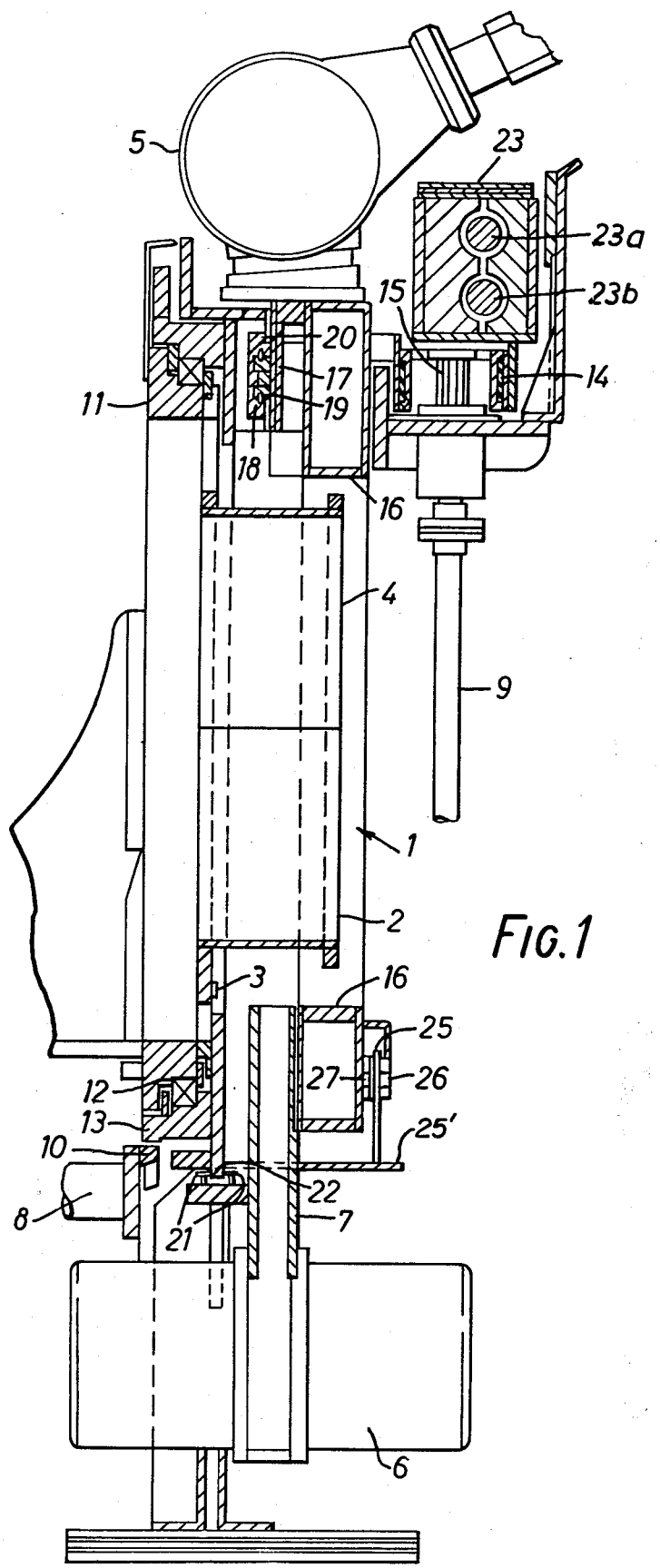

United States Patent [19]

Hounsfield et al.

[11] 4,066,906

[45] Jan. 3, 1978

[54] SCANNING RADIOGRAPHIC APPARATUS

[75] Inventors: Godfrey Newbold Hounsfield, Newark; Peter George Langstone, Gerrards Cross, both of England

[73] Assignee: EMI Limited, London, England

[21] Appl. No.: 692,182

[22] Filed: June 2, 1976

[30] Foreign Application Priority Data

June 11, 1975 United Kingdom ............... 25112/75

[51] Int. Cl.² ........................................... G01N 23/00
[52] U.S. Cl. ................................................ 250/445 T
[58] Field of Search ................ 250/445 T, 360, 237 G

[56] References Cited

U.S. PATENT DOCUMENTS 3,965,357  6/1976  Hounsfield .......................... 250/360
3,973,119  8/1976  Remes et al. ...................... 250/237 G Primary Examiner—Bruce C. Anderson
Attorney, Agent, or Firm—Cooper, Dunham, Clark, Griffin & Moran

[57] ABSTRACT

In a scanning radiographic apparatus in which the object of the scanning is to project the radiation through a substantially planar region of a body along many linear paths, means is provided for monitoring the progress of the scanning and producing timing signals indicative thereof. The timing signals are used to determine, at least in part, the widths of the aforementioned beams and a characteristic, for example the frequency in the event that the signals comprise pulses, is changed to permit the effective width of the paths to be changed. This can be done by means of graticules having differently pitched markings, for example, and each graticule may be associated with a respective range of body sizes.

10 Claims, 2 Drawing Figures

SCANNING RADIOGRAPHIC APPARATUS

The present invention relates to radiographic apparatus, and it relates more especially to such apparatus for providing a representation of the variation in absorption of the penetrating radiation used with position over a planar, cross-sectional area of a body.

Such apparatus has been described in U.S. Pat. No. 3,778,614 and in U.S. Pat. No. 3,946,234.

From these specifications it will be appreciated that the principle of operation involves scanning a source of penetrating radiation and a detector means (comprising one or more detectors) relative to a body in the plane of interest. The scanning is arranged so that the body is irradiated along a plurality of co-planar paths, many of which intersect within the body. The absorption suffered by the radiation on traversing each path is recorded and used in a computation process to evaluate the absorption coefficient attributable to each element of a two-dimensional matrix of elements notionally delineated in the plane of interest.

In order to irradiate the body along each of the aforementioned paths, it has been found convenient to scan the source and detector means linearly relative to the body, then to rotate the source and detector means through a predetermined angle about an axis perpendicular to the plane of interest and then to scan the source and detector means linearly relative to the body in approximately the opposite direction to the previous linear scan. This procedure of alternate linear scans and predetermined increments of rotation is continued until a total rotation of about 180° or more has been achieved.

In order that the computation can be carried out with accuracy, it will be appreciated that it is necessary for the position of the source and detector means to be accurately monitored during the scanning procedure, so that the data signals relating to absorption of radiation on traversing the various paths can be identified and used at the correct stage in the computation process.

Particularly in apparatus, such as that described in U.S. Pat. No. 3,946,234, for examining the torsos of human patients, it is necessary to provide for considerable variation in the cross-sectional dimensions of the body as between different patients. It has been found to select one of a number of differently sized rings to surround the body at the plane of interest to locate patients in the apparatus; an oversized ring being chosen as appropriate for each patient, and the region between ring and the body being filled with an appropriate medium having absorption qualities similar to those of human tissue.

If the apparatus were used with no further modifications, the representations obtained for small bodies would be displayed with a spatial resolution equal to that obtainable for large bodies, whereas it would be desirable for the resolution to vary with the dimensions of the body. The object of this invention is to provide apparatus capable of achieving this in an advantageous way.

According to the invention there is provided radiographic apparatus including means defining a patient position, a source of penetrating radiation, such as X-radiation, arranged to project said radiation through said patient position along at least one beam path, scanning means for scanning the source of said radiation relative to the patient position so as to project said radiation therethrough along further beam paths displaced angularly and/or laterally from said at least one beam path, a sensing arrangement for sensing the progress of said scanning and for providing timing signals indicative thereof, detecting means including at least one detector device for detecting the amount of said radiation emergent from said patient position along each of said beam paths and for producing output signals indicative of said amounts, circuit means connected to receive said timing signals and said output signals and adapted to utilise said timing signals to determine, at least in part, the effective widths of said beam paths to which said output signals relate, and means for varying a characteristic of said timing to change the effective widths of said paths.

Figure 2:
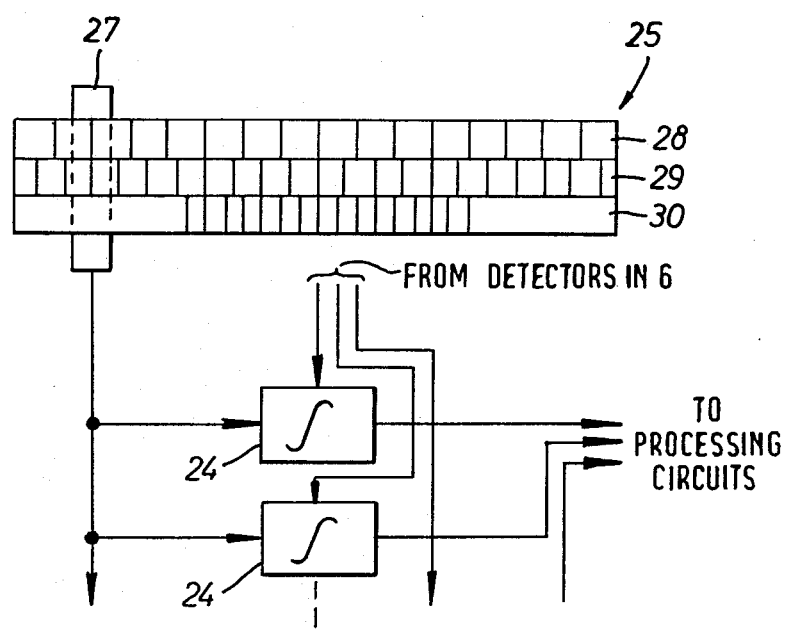

In order that the invention may be clearly understood and readily carried into effect, one embodiment thereof will now be described, by way of example only, with reference to the accompanying drawings of which:

FIG. 1 is a general side elevational view, partly in cross-section, of apparatus in accordance with one example of this invention, and FIG. 2 shows, in block schematic form, part of the apparatus in accordance with one example of this invention.

Referring now to FIG. 1 of the drawings, a patient (not shown) to be examined is constrained to lie with the relevant part of his body disposed within a locating collar 1. The collar 1 is formed of a lower half 2, which is releasably secured to a fixed part of the apparatus, for example by means of bolts such as 3, and an upper half 4 which is secured to the lower half once the patient is in position. A bag (not shown) containing a medium which absorbs radiation to an extent similar to that of human tissue is wrapped around the body and trapped between the collar 1 and the patient's body so as to exclude air, as far as possible, from the periphery of the section of the body which is to be examined.

A source 5 of X-radiation, and an associated detector arrangement 6 with associated collimator means 7 are disposed on either side of the collar 1. These components are arranged to execute rotational and translational scans relative to the collar by means of respective electric motors (not shown) which drive shafts 8 and 9 respectively. Shaft 8 drives a pin member 10 which constitutes part of a geneva mechanism for effecting the rotational scan, the scan being carried out in angular steps of a few degrees. The remainder of the geneva mechanism comprises a fixed ring 11, which carries an annular bearing 12 around which a movable, toothed ring 13 can move, such motion of course being in a plane perpendicular to the plane of the paper. The ring 13 carries with it, as it rotates, a frame upon which are mounted the components which are used for effecting the translational scan, including the electric motor which drives the shaft 9. This motor is a reciporcating motor.

Shaft 9 drives an endless, toothed rubber belt 14 by means of a toothed drive wheel 15; the belt 14 extending out of the plane of the paper passing over a toothed idler wheel (not shown). Attached to the belt 14 at one side of the wheel 15 and the idler wheel is a yoke 16, of elongated oval shape in elevation, which carries the X-ray source 5 and the detector/collimator assembly, 6 and 7. The yoke 16 carries a frame 17 bearing rollers such as 18 which run in grooved, linear tracks 19 formed in a member 20 attached to the ring 13. The member 20 thus rotates with ring 13 but does not take part in the translational scan; the yoke 16 being arranged to translate relative to it. Fore-and-aft movement of the yoke 16 (i.e. left-to-right movement in FIG. 1) is restricted by means of a pair of rollers 21 which roll on a plate member 22 which, like the member 20, rotates but does not take part in the translation scanning.

In order to maintain an even distribution of mass despite the fact that the source 5 takes part in the translational scanning, a counter-balance weight 23 is secured to the opposite side of belt 14 to the yoke 16 and thus executes lateral scans in the opposite direction to the source 5. The weight 23 runs on a pair of rods 23a, 23b.

The sequence of events is thus that the yoke 16 and its attachments (including the source 5 and the detector arrangement 6) are caused to execute a first lateral scan relative to the collar 1; the ring 13 and its attachments (including the yoke 16) are rotated through an angle of (say) ten degrees relative to the collar; the yoke 16 and its attachments then execute a second lateral scan relative to the aperture, this scan being in substantially the opposite direction to the first lateral scan, this being followed by a second rotational step of ring 13 and its attachments, and so-on until the total angular movement of ring 13 is about 180° or more.

The source 5 is arranged to produce a fan-shaped sheet of radiation which extends above and below the plane of the paper, the angle of the fan being, for example, 10°. The detector arrangement 6 includes a plurality of radiation sensitive detectors, each responsive to radiation travelling along a respective radial path in the aforementioned sheet, and in one example thirty such detectors are provided. The radiation which can be received by each detector is defined by a respective collimator in the collimator means 7. As a lateral scan proceeds, each detector provides output signals relating to the amount of radiation passed through the body along a plurality of different paths; the width of each path being determined by electrical timing pulses which are produced during each lateral scan and used to control the integration time of integrator circuits, such as 24 in FIG. 2, which are provided for each detector in the detector arrangement 6. The integrators such as 24 feed processing circuits (not shown) arranged to process the data to provide a representation of the variation, with position across the planar slice of interest through the patient's body, of absorption of the X-radiation from the source 5. Such processing will not be described further herein, since it forms no part of this invention, but examples of suitable processing arrangements can be found in U.S. Pat. No. 3,778,614 and in U.S. Pat. No. 3,924,129.

The aforementioned electrical timing pulses are derived, in this example, by means of a graticule member 25, which comprises a translucent member bearing equally spaced opaque lines, and lamp and photocell detector units 26, 27. The member 25 is mounted, by means of a bracket 25', to a part of the apparatus which rotates, but does not take part in the translational scanning. It is therefore fixed in relation to the yoke 16, which carries the units 26 and 27 which thus scan along the graticule member 25 during each lateral scan.

As can be seen more clearly in FIG. 2, the graticule member 25 in fact carries three graticules, 28, 29 and 30, the opaque lines of which are of different pitches. Units 26 and 27 include respectively three lamps and three photocells, one lamp and one cell for each graticule. The reason for providing three graticules and three lamp/detector units is that it is usual to provide an apparatus with three collars such as 1 (FIG. 1) to accommodate different patient sizes. The diameters of the collars are, respectively, 16, 13 and 10 inches. As mentioned in the introduction, it is desirable for the spatial resolution of the representation produced by the apparatus to vary with the dimensions of the body being examined, and this is achieved, in this example, by varying the frequency of the timing pulses derived from the units 26 and 27 in accordance with the size of the collar used. This is done by deriving the timing pulses from a respective one of the three graticules 28, 29 and 30 in dependence upon the collar size; the 16 inch collar being associated with graticule 28, the 13 inch collar with graticule 29 and the 10 inch collar with graticule 30. The selection is achieved by selectively energising the lamp and photocell unit associated with the relevant graticule and de-energising the other two units.

In practice, when either the 16 inch or 13 inch collars are in use the linear traverse motor is operated at the same speed and the yoke 16 and its attachments are scanned across the full extent of the linear traverse; the timing pulse rate being higher for the 13 inch collar than for the 16 inch collar, however, because of the smaller pitch of the opaque lines on graticule 29 as compared with those on graticule 28. This means that the integration times for the 16 inch collar are somewhat longer than those for the 13 inch collar, so that the resolution in the former case is somewhat lower than the latter case. This, however, is acceptable because of the larger dimensions of the body accommodated in the 16 inch collar.

In the case of the 10 inch collar, the traverse may be carried out at the same speed as for the two larger collars, or a lower speed could be used if desired, but in any event the linear scan is not allowed to procede to its extremities, since this would entail an unacceptable degree of wasted time when the radiation was not within the bounds of the body. The early termination and reversal of the linear scan under these conditions may be achieved, for example, by a mechanical stop or buffer which is manually set into position when a 10 inch collar is used, or it could be effected electrically if the graticule were provided with suitable end of scan markings which, when scanned by the respective photocell unit, could provide a reversing signal for application to the translation motor. It will be observed that the pitch of the opaque lines on the graticule 30 is finer than those on either of the other graticules, and whether the scan is effected at the same speed as for the two larger collars, or at a lower speed, the arrangement is such that the timing pulses are of higher frequency than would be provided by graticules 28 and 29, so providing a higher definition. An advantage of using a slower scanning speed is that more X-radiation can be passed through the body, subject of course to maintaining safe dosage limits, and thus better accuracy can be obtained in the resultant representation.

A counter (not shown) of conventional kind can be provided to count the timing pulses and to initiate reversal of the lateral-scan when a predetermined number (e.g. 160) of the pulses have been counted.

Alternatively the reversal may be effected by other means, and the counter merely used to provide an indication to the processing circuits of the number of beam paths irradiated during each lateral scan.

It will be appreciated that the foregoing embodiment of the invention has been described by way of example only and that other embodiments not departing from the scope of this invention may be devised by those skilled in the art.

What I claim is:

1. Radiographic apparatus including means defining a patient position, a source of penetrating radiation, such as X-radiation, arranged to project said radiation through said patient position along at least one beam path, scanning means for scanning the source of said radiation angularly and laterally relative to the patient position so as to project said radiation therethrough along further beam paths displaced angularly and/or laterally from said at least one beam path, a sensing arrangement for sensing the progress of said lateral scanning and for providing timing signals indicative thereof, detecting means including at least one detector device for detecting the amount of said radiation emergent from said patient position along each of said beam paths and for producing output signals indicative of said amounts, circuit means connected to receive said timing signals and said output signals and adapted to utilise said timing signals to determine, at least in part, the effective widths of said beam paths to which said output signals relate, and means for varying a characteristic of said timing signals to change the effective widths of said paths.

2. Apparatus according to claim 1 wherein said sensing arrangement includes means for generating regularly occurring electrical impulses, which constitute said timing signals, and wherein the said characteristic of said timing signals which is varied by said means for varying is the inter impulse period.

3. Apparatus according to claim 2 wherein said sensing means includes a graticule, a lamp and photocell circuit and means for causing relative movement, concomitantly with the scanning of the source relative to the patient position, between the graticule on one hand and the lamp and photocell circuit on the other hand, to generate said electrical impulses at the photocell circuit.

4. Apparatus according to claim 3 wherein said means for varying includes an element of said scanning means which is arranged to change the speed of said scanning.

5. Apparatus according to claim 3 wherein said sensing means includes a plurality of graticules and respective lamp and photocell circuits each capable of generating, for a given speed of operation of said scanning means, timing impulses at a respective, substantially constant rate, said means for varying including selector means for selecting the timing impulses generated at one of said photocell circuits.

6. Apparatus according to claim 1 wherein said scanning means scans said source successively in lateral sweeps and angular steps relative to the patient position, the total angular movement being at least about 180°.

7. Apparatus according to claim 1 wherein said source comprises an X-ray tube and said scanning means includes means for physically scanning said tube relative to said patient position.

8. Apparatus according to claim 1 wherein said scanning means is also effective to scan said detecting means relative to said patient position.

9. Apparatus according to claim 8 wherein said source is arranged to produce a substantially planar, fan-shaped spread of radiation and said detecting means comprises a plurality of closely packed detector devices distributed across the full extent of the spread.

10. Apparatus according to claim 9 wherein said scanning means is effective to cause said source and said detector means to concomitantly execute alternate lateral sweeps and angular steps relative to said patient position, the angular steps being carried out about an axis substantially perpendicular to said spread of radiation and being of magnitude which takes into account the angle of the fan-shapedspread.

* * * * *